United States Patent [19]

Chou et al.

[11] Patent Number: 4,602,118

[45] Date of Patent: Jul. 22, 1986

[54] LIQUID PHASE OXIDATION OF ORGANIC COMPOUNDS TO THEIR HYDROPEROXIDES

[75] Inventors: Mau-Song Chou, Mountainside; Keith W. Wohltman, Basking Ridge, both of N.J.

[73] Assignee: Exxon Research and Engineering Co., Florham Park, N.J.

[21] Appl. No.: 669,898

[22] Filed: Nov. 9, 1984

[51] Int. Cl.$^4$ ............................................ C07C 179/02
[52] U.S. Cl. .................... 568/570; 568/571; 568/573
[58] Field of Search ................ 568/570, 571, 573, 569

[56] References Cited

U.S. PATENT DOCUMENTS

| | | | |
|---|---|---|---|
| 2,367,666 | 3/1941 | Carleton | 106/220 |
| 2,577,768 | 12/1951 | Joris | 568/573 |
| 2,674,629 | 4/1954 | Seriabine | 568/573 |
| 2,680,139 | 6/1954 | Fenpglio et al. | 568/573 |
| 2,749,368 | 6/1956 | Fortuin et al. | 568/574 |
| 2,792,424 | 5/1957 | Weesner | 568/573 |
| 2,792,425 | 5/1957 | Weesner | 568/573 |
| 2,792,426 | 5/1957 | Weesner | 568/573 |
| 2,845,461 | 7/1958 | Winkler et al. | 568/571 |
| 2,861,107 | 11/1958 | Hiratsuka et al. | 568/573 |
| 2,913,277 | 11/1959 | Adell | 296/44 |
| 2,955,996 | 10/1960 | Mashio et al. | 568/574 |
| 2,973,310 | 2/1961 | Whitfield | 568/573 |
| 3,113,085 | 12/1963 | Besancon et al. | 568/571 |
| 3,539,645 | 11/1970 | Mead | 563/573 |

FOREIGN PATENT DOCUMENTS

| | | | |
|---|---|---|---|
| 1239348 | 7/1959 | France . | |
| 4973 | 2/1970 | Japan | 568/573 |
| 45-4973 | 2/1970 | Japan | 568/573 |
| 665897 | 1/1952 | United Kingdom . | |
| 801347 | 9/1958 | United Kingdom . | |
| 0642305 | 1/1979 | U.S.S.R. | 568/569 |

OTHER PUBLICATIONS

Hall, "Laser in Industrial Chemical Synthesis", Sep., 1982, Laser Focus, pp. 57-62.
Kulicki, et al., *Rocz. Chem. 1971*, 45(4), pp. 601-606.
Antonovskii et al., *Russian J. Chem.*, 3, 232 (1967).
Sauer et al., *J. Phys. Chem.*, 75, (1971), 3377.
Hiatt, *Frontiers of Free Radical Chemistry*, Acad. Press, New York, 1980, p. 225.
Hendry et al., Symposium on Oxidation Studies, Atlantic City, p. 636 (1974).
Denisov, *Russ. J. Phys. Chem.*, 37, 1029 (1963).
J. A. Howard, "Free Radicals", vol. 2, Ch. 12, John Wiley, New York (1973).
SRI Report No. 22B, "Cumene Hydroperoxide Process" (1978).
Chapman, *Organic Photochemistry*, vol. 2, pp. 34-37, 1969, Marcel Dekker, New York.
Kan, Organic Photochemistry, p. 23, 1966, McGraw-Hill, New York.

*Primary Examiner*—Werren B. Lone
*Attorney, Agent, or Firm*—E. Thomas Wheelock

[57] ABSTRACT

This invention deals with a process for the production of hydroperoxides from their corresponding hydrocarbons via the use of certain ketones, particularly aryl ketones, generally having strong substituent electrophilic groups, as promoters. These promoters increase the rate of thermal oxidation and improve selectivity to the hydroperoxide products.

2 Claims, No Drawings

LIQUID PHASE OXIDATION OF ORGANIC COMPOUNDS TO THEIR HYDROPEROXIDES

FIELD OF THE INVENTION

This invention deals with a process for the production of hydroperoxides from their corresponding hydrocarbons via the use of certain ketones, particularly aryl ketones, generally having strong substituent electrophilic groups, as promoters. These promoters increase the rate of thermal oxidation and improve selectivity to the hydroperoxide products.

BACKGROUND OF THE INVENTION

Several hydroperoxides have important uses in various chemical processes. For example, ethylbenzene hydroperoxide and t-butyl hydroperoxide are used in the epoxidation of propylene to form propylene oxide. When propylene epoxidation is carried out with ethylbenzene hydroperoxide, styrene is also formed as a co-product. The cleavage of cumene hydroperoxide leads to the formation of phenol and acetone.

The hydroperoxides may be prepared by free radical chain reactions wherein the base compound, e.g., cumene, is oxidized with air or oxygen to form the corresponding hydroperoxide. To increase conversion efficiency catalysts and promoters are generally utilized. Various modifications of this common process for the production of hydroperoxides are disclosed in the art.

The starting material for hydroperoxide formation typically is an organic compound, which may be substituted or unsubstituted, having at least one secondary or tertiary hydrogen. Compounds having tertiary hydrogens are more readily oxidized to the hydroperoxide.

Illustrative of processes for the production of cumene hydroperoxide is the method disclosed in U.S. Pat. No. 2,577,768 (1951). Cumene is oxidized to the corresponding hydroperoxide by bubbling air into a mixture of cumene and $NaHCO_3$ which is used as a catalyst. The reaction is carried out at 75° C. A 26% conversion after 72 hours is alleged.

The use of heavy metal catalysts to improve conversion efficiencies is disclosed in British Pat. No. 665,897. The catalyst is a compound of Mn, V, Co, Pb, Ni, Fe, Cu, Cr or Hg. The preferred compounds are the oxides, hydroxides or organic acid salts which are soluble in the organic compound to be oxidized, e.g, cumene. Conversion of 58% at 45° C. is alleged.

Other catalysts disclosed in the art for alkyl hydroperoxide production include $CaCO_3$ (U.S. Pat. No. 2,913,277), phthalorganic salts (British No. 801,347), ethylenediamine tetraacetic acid (U.S. Pat. No. 2,861,107) and arylisobutyronitrile (Ger. offen. No. 2,035,504).

The use of elevated temperatures to produce hydroperoxides is often disadvantageous since side reactions may occur and the hydroperoxide is decomposed. Picoline, pyrrole or thiophene are disclosed as side reaction inhibitors. See Japanese Pat. No. 58045. Similarly the art teaches that copper, silver and gold will act as inhibitors for that decomposition. See, for example, U.S. Pat. No. 2,820,832.

A typical method for the preparation of ethylbenzene hydroperoxide is disclosed in U.S. Pat. No. 2,749,368. The process is similar to that for cumene hydroperoxide formation. Copper is utilized as a catalyst and the reaction temperature is about 50° C. below the boiling temperature of the hydrocarbon being oxidized. Other related processes are alkali metal carbonates, bicarbonates and oxides as catalysts for the preparation of ethylbenzene hydroperoxide; see U.S. Pat. No. 2,367,666.

Tertiary butyl hydroperoxide is of considerable commercial importance and is widely used as a free-radical initiator for polymerization processes. It can be prepared non-catalytically by the auto oxidation of isobutane at about 100° C. to about 150° C. in a metal ion free reaction medium at a pressure of about 400 psig; see U.S. Pat. No. 2,845,461. The catalysts which are disclosed as being useful in the preparation of cumene hydroperoxide and ethylbenzene hydroperoxide may be advantageously utilized in the preparation of t-butyl hydroperoxide.

There have been various attempts to avoid the use of elevated temperatures by utilizing free radical initiators other than heat, e.g., radiation and photon sources. For example, U.S. Pat. No. 3,113,085 (1963) discloses that conversion rates of 26% can be achieved in the production of cumene hydroperoxide at a dose rate of 100 rad/min. The temperature is maintained below 70° C., the decomposition temperature of the hydroperoxide.

French Pat. No. 1,239,348 (1960) discloses the photo oxidation of cumene to cumene hydroperoxide utilizing a mercury vapor lamp as the photon source and benzophenone as a photochemical sensitizer. Similarly, U.S. Pat. No. 2,973,310 discloses the use of an ultra violet (UV) light source in conjunction with a free radical initiator, e.g., $Ba(OH)_2$. Titanium dioxide is disclosed as a suitable catalyst for the photo oxidation of cumene using a UV source of about 3000–4000 Å wavelengths. The reaction is carried out at 25° C. to 130° C.; see U.S. Pat. No. 2,955,996 (1960).

Recently, the use of lasers to produce hydroperoxides from cumene was described in an article by R. B. Hall, "Laser In Industrial Chemical Synthesis", September, 1982, *Laser Focus*, pp. 57–62. The disclosure is of the work of the instant inventors.

In a similar vein, there exist a number of publications suggesting various accelerators in the oxidation of hydrocarbons to their hydroperoxide analogs.

The process shown in U.S. Pat. No. 2,674,629, issued Apr. 6, 1954, to Scriabine, begins with cumene or "other aliphatic-aromatic hydrocarbons" and prepares hydroperoxides of those beginning compounds by subjecting the feed material to treatment in the liquid phase with oxygen at an elevated temperature in the presence of a β-ketonic ester. The ester preferably is ethyl acetoacetate or ethyl benzoylacetate.

Similarly, the process in U.S. Pat. No. 2,792,424, issued May 14, 1957, to Weesner synthesizes various hydroperoxides of cumene, ethylbenzene, diphenylmethane and the like at high temperatures in liquid phase using oxygen and a β-diketone which is free from ester groups in a position which is beta to the keto group. The preferred initiator apparently is 2,4-pentanedione.

In U.S. Pat. No. 2,797,425, issued May 14, 1957 also to Werner, the oxidation initiators disclosed are the esters of malonic acid or of substituted malonic acid. The preferred class includes those malonic esters which has at least one hydrogen atom on the carbon atom joining the two ester or carboalkoxy groups. The apparently preferred initiators are diethyl malonate or diethyl (isobutyl) malonate.

In Kulicki et al, *Rocz. Chem.* 1971, 45(4), pp. 601–6, the effect of the accelerators acetophenone and dimethylphenylcarbinol on the 1,1-azobis-(1-cyclohexanenitrile) initiated or cumene hydroperoxide initiated oxidation of cumene to cumene hydroperoxide was studied. Both accelerators were said to promote the cumene hyperoxide initiated reaction although the effect of dimethylphenylcarbinol was more pronounced.

None of these publications show the use of a ketone as a promoter in the liquid phase reaction of hydrocarbons to the hydroperoxide form and wherein the promoter activity of the ketone is greater than acetophenone.

SUMMARY OF THE INVENTION

This invention relates to a process for the production of hydroperoxides from their corresponding hydrocarbons via the use of certain ketones, generally aryl-substituted ketones and/or ketones having strongly electrophilic substituent groups, as promoters in the liquid phase reaction. The promoter ketone must produce an enhanced reaction rate and a selectivity greater than that obtained from acetophenone. The most desirable promoter is benzophenone although others such as (ortho-$(NO_2)$) $(C_6H_4)_2C=O$, (meta-$(NO_2)$) $(C_6H_4))_2C=O$, $(C_6F_5)_2C=O$, $(CF_3)_2C=O$ are suitable.

The inventive process is considered to be operable on most hydrocarbons. However, the most important entail the reactions of: cumene to cumene hydroperoxide, ethylbenzene to ethylbenzene peroxide, isobutane to t-butyl hydroperoxide, and cyclohexane to cyclohexanylhydroperoxide.

DETAILED DESCRIPTION OF THE PREFERRED EMBODIMENTS

This invention relates to a process for the preparation of hydroperoxides from their analagous hydrocarbon compounds in the liquid phase via the use of certain ketones as promoters. The ketones are generally aryl ketones but in any event are those having substitutent groups, often highly electrophilic, thereon which result in a reaction rate increase greater than the increase resulting from the use of acetophenone in the same hydrocarbon/hydrocarbon hydroperoxide system. The selected ketones improve the selectivity of the system to the hydroperoxide product as well as increasing the reaction rate.

Although not wishing to be bound by theory, the promotion of thermal oxidation of hydrocarbons to hydrocarbon hydroperoxides using gaseous oxygen in the liquid phase is thought to be due to the formation of an adduct between the ketones and the hydroperoxides. These promoters may be postulated as via adducts between ketones and hydroperoxides:

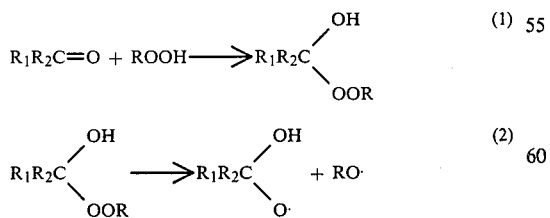

where ROOH is a hydroperoxide, and $R_1$ and $R_2$ are functional groups of a ketone, $R_1R_2C=O$. Since the O—O bond in peroxides ($\approx 38$ Kcal/mole) is substantially weaker than that in hydroperoxides ($\approx 41$ Kcal/mole), the adducts can lead to an increased initiation rate as compared to that of free hydroperoxides in the thermal reaction:

$$RO OH \rightarrow RO \cdot + OH \cdot \quad (3)$$

The adducts between aldehydes and hydroperoxides have been observed spectroscopically in various solvents. For example, Antonovskii, et al., *Russian J. Chem.*, 3, 232 (1967) using infrared methods, identified the adduct between t-butyl hyderoperoxide and acetaldehyde in $CCl_4$, $CHCl_3$, and i-$Pr_2O$. Sauer, et al., *J. Phys. Chem.*, 75, 3377 (1971) and Hiatt, *Frontiers of Free Radical Chemistry*, pg. 225, Acad. Press, New York, 1980, using a NMR technique, identified the same adduct in benzene. It has been shown that cyclohexanone accelerates the oxidation of cyclohexane, and this effect is attributed to the formation of an adduct between cyclohexanone and cyclohexanyl hydroperoxide, Hendry et al, Symposium on Oxidation Studies, Atlantic City, N.J., pp. 636 (1974) and Penison, *Russ J. Phys. Chem.*, 37, 1029 (1963). Using infrared methods, Denison confirms the formation of an adduct between cyclohexanone and t-butyl hydroperoxide. Hiatt postulated an adduct between ketone and hydroperoxide in alcoholic solvents to account for the decomposition rates of t-$BuO_2H$ and s-$BuO_2H$ in MeOH with the addition of acetone, methylethyl ketone, or diethyl ketone. In general, Hiatt considers a ketone-hydroperoxide adduct to be less favorable in a non-polar solvent. In this work, we have shown that certain ketones which have strongly electrophilic functional groups, such as aryl, promote hydrocarbon oxidations even in non-polar media.

The autoxidations of cumene and ethylbenzene involve free-radical chain reactions and have been discussed extensively. See, J. A. Howard, "Free Radicals", Vol. 2, Chapter 12, ed. by J. K. Kochi, John-Wiley, New York (1973); Chem. Systems Report No. 80-3, "Styrene", (1980); and SRI Report No. 22B, "Cumene Hydroperoxide Processes" (1978). The main reaction steps may be summarized as:

Initiation: Radical generation

Propagation: $R \cdot + O_2 \rightarrow RO_2 \cdot$ \hfill (4)

$RO_2 \cdot + RH \rightarrow RO_2H + R \cdot$ \hfill (5)

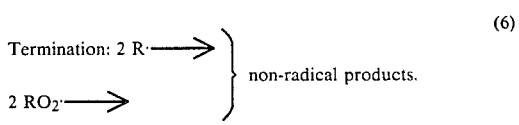

(6)

In a non-promoted autoxidation reaction, the initiation is thought to be the homolysis of O—O bond as shown in Reaction (3) followed by hydrogen abstraction:

$RO \cdot + RH \rightarrow ROH + R \cdot$ \hfill (7)

$OH \cdot + RH \rightarrow H_2O + R \cdot$ \hfill (8)

The promotion by the selected ketones may be explained in terms of the homolysis of the adduct (Reaction 2) then react rapidly with hydrocarbons (Reactions 8 and 9) and thereby initiate chain propagation.

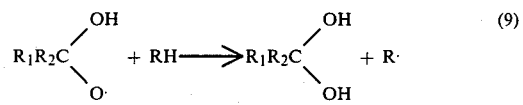

(9)

The formation of ketone-hydroperoxide adducts is generally unfavorable in hydrocarbon media. However, if $R_1$ and/or $R_2$ are strong electrophilic groups, the stability of the adduct may be enhanced resulting in higher adduct formation rate. The inductive effect of the functional groups may rationalize the observed reactivity order (as is demonstrated in the examples below): benzophenone>>acetophenone>>9-fluoroenone in the oxidation of cumene and ethylbenzene.

The formation of adducts is further suggested by the comparison of the infrared spectrum of a mixture of benzophenone and cumene hydroperoxide in pentane to those of cumene hydroperoxide in pentane. It shows that the peak intensity of the hydroperoxide bending vibrational mode at 835 cm$^{-1}$ is reduced when benzophenone is added.

The increase in hydroperoxide selectivity with these ketones is of substantial interest. It is known that conventional catalysts, such as transition metal ions, often result in degradation of selectivity.

In any event, the use of the ketones specified herein may be used in the synthesis of most hydroperoxides from their analogous hydrocarbons. However, the hydrocarbons are desirably selected from the group consisting of cumene, ethylbenzene, isobutane and cyclohexane or any one of these.

The promoter ketone generically is any ketone which produces an enhanced reaction rate in the hydroperoxidation reaction greater than that produced by acetophenone upon the same hydrocarbon. The most desirable promoter is benzophenone but others may be selected from the group of (ortho-$(NO_2)(C_6H_4))_2C=O$, (meta-$(NO_2)(C_6H_4))_2C=O$, $(C_6F_5)_2C=O$, and $(CF_3)_2C=O$.

The reaction conditions include operation at a sufficiently high temperature to produce the hydroperoxidation reaction on the particular hydrocarbon. Usually a temperature between 100° C. and 200° C. is required while maintaining the liquid phase. Between about 100° C. and about 150° C. is a desirable range.

The oxygen used in the reaction may be pure or in admixture with other typically non-reactive gases, e.g., in the form of air. The amount of oxygen-containing gas is not particularly critical.

EXAMPLES

The promotion of the aromatic ketones in the oxidation of organic compounds to form their corresponding hydroperoxides is illustrated in the following examples. The oxidation reactions were carried out in the specified cylindrical aluminum or TEFLON cells. Each cell had a diameter of 1.9 cm and a length of 3.8 cm. Prior to each experiment the cells were degreased and cleaned using various reagents. For the aluminum cell, the degreasing and cleansing agents included methanol, acetone, $Na_2CO_3$ and acid bright-dip with subsequent rinsing with distilled water. When the aluminum cell was used in its uncoated form, it was dried in a nitrogen glove box. When it was coated with sodium pyrophosphate ($Na_4P_2O_7$), the coating was applied by rinsing the cell with a saturated solution of $Na_4P_2O_7$ and drying in an oven at about 100° C. Samples of the liquid in the reactor were withdrawn at various reaction times through a septum port and subjected to G.C. analysis. The gas chromatography columns used were glass capillary columns coated with methyl silicone (Hewlett-Packard, cross-linked) or phenylmethylsilicone (J & W, SE-54).

Cumene (Fluka, AG, 99.51%), ethylbenzene (MCB, 99%) and Linde oxygen (99.5%) were used, as received, without further purification. Gas chromatographic analysis of feed samples showed that the initial cumene sample contained 0.24% cumene hydroperoxide and 0.01% acetophenone, whereas the ethylbenzene samples contained 0.48% ethylbenzene hydroperoxide and 0.1% acetophenone.

EXAMPLE 1

The $Na_4P_2O_7$ coated aluminum cell was charged with 12 ml. of cumene and maintained at 120° C. using a temperature regulated oil bath. Oxygen was bubbled through the liquid at about 0.2 l/min. through an array of pinholes in the test cell wall. The gas pressure above the liquid was maintained at 2.8 atm. The oxidation of cumene to cumene hydroperoxide was carried out for the following two cases: (1) no benzophenone promotion, and (2) with benzophenone (0.42wt.%) added at the beginning of the experiment. The results are summarized in Table 1. The cumene conversion was substantially higher with the benzophenone promoter. In addition, the selectivity to cumene hydroperoxide was slightly improved as compared to that without the additive for the same extent of conversion.

The $Na_4P_2O_7$ coating was used to minimize the wall reaction and also to neutralize any acidic byproducts produced during the oxidation process.

TABLE 1

| Cumene Oxidation in $Na_4P_2O_7$ Coated Aluminum Cell | | | |
|---|---|---|---|
| | Time, hr | Conversion, % | Selectivity to Hydroperoxide |
| No additive | 0.5 | 0.7 | 94 |
| | 1.0 | 2.1 | 95 |
| | 2.0 | 4.1 | 90 |
| | 3.0 | 8.5 | 88 |
| 0.42% Benzophenone added | 0.5 | 0.64 | 100 |
| | 1.0 | 1.8 | 99 |
| | 1.5 | 4.0 | 95 |
| | 2.0 | 6.4 | 94 |
| | 3.0 | 15.2 | 92 |

EXAMPLE 2

The experiments of Example 1 were repeated using an uncoated aluminum cell for various amounts of benzophenone promoter. The results are summarized in Table 2. The cumene oxidation rate and the selectivity to cumene hydroperoxide were decreased in the uncoated cell as compared to that in the coated cell as shown in Example 1. Large amounts of phenol and α-methyl styrene by-products were also present, especially in the case without the promoter. These by-products are considered to inhibit the oxidation rate and their build-up during the reaction may be responsible for the observed poor selectivity to the hydroperoxide. These by-products are believed formed by the wall reactions in the uncoated aluminum cell.

Even in the presence of the wall degradation problem in the uncoated cell, the benzophenone promoter substantially improved the rate of oxidation and the selectivity to the hydroperoxide as compared to that without the additive. In addition, the by-products of phenol and α-methyl styrene were substantially reduced as compared to that without the promoter for the same extent of conversion. The optimal benzophenone concentration appeared to be ~1.2 wt.%.

TABLE 2

Cumene Oxidation in Uncoated Aluminum Cell

|  |  |  | Hydroperoxide | By-product Distribution, % | |
|---|---|---|---|---|---|
|  | Time, hr | Conversion, % | Selectivity, % | Phenol | α-Methylstyrene |
| No additive | 1 | 0.15 | 89 | 1.3 | 2.0 |
|  | 2 | 0.54 | 91 | 2.4 | 2.3 |
|  | 3 | 0.97 | 90 | 4.6 | 2.3 |
|  | 4 | 1.4 | 86 | 6.1 | 3.6 |
|  | 5 | 1.7 | 79 | 10.3 | 4.0 |
| 0.17% Benzophenone | 1 | 1.2 | 93 | 1.6 | 1.9 |
|  | 2 | 2.3 | 86 | 4.0 | 1.7 |
|  | 3 | 2.3 | 80 | 8.1 | 3.1 |
| 0.30% Benzophenone | 1 | 1.7 | 94 | 1.1 | 0.8 |
|  | 2 | 2.6 | 92 | 2.9 | 1.5 |
|  | 3 | 2.9 | 86 | 5.3 | 2.2 |
| 1.2% Benzophenone | 1 | 1.8 | 96 | 0.5 | 0.8 |
|  | 2 | 3.4 | 84 | 6.5 | 2.8 |
|  | 3 | 3.4 | 85 | 5.1 | 2.8 |
| 2.3% Benzophenone | 1 | 1.3 | 94 | 0.8 | 0.7 |
|  | 2 | 2.1 | 92 | 2.7 | 1.4 |
|  | 3 | 2.5 | 96 | 7.0 | 2.8 |

EXAMPLE 3

The experiments of Example 2 were repeated substituting ethylbenzene for cumene as the feed. The uncoated aluminum cell was maintained at 150° C. Table 3 shows that the benzophenone promoter (1.3 wt.%) increased the ethylbenzene oxidation rate and the selectivity to ethylbenzene hydroperoxide, and also reduced the by-products of phenol and styrene as compared to that without the promoter.

TABLE 3

Ethylbenzene Oxidation in Uncoated Aluminum Cell

|  |  |  | Hydroperoxide | By-Product Distribution, % | |
|---|---|---|---|---|---|
|  | Time, hr | Conversion, % | Selectivity, % | Phenol | Styrene |
| No additive | 1 | 2.0 | 45 | 7.7 | 0.9 |
|  | 2 | 3.9 | 34 | 13.0 | 1.5 |
|  | 3 | 4.7 | 28 | 17.0 | 2.1 |
|  | 4 | 5.7 | 19 | 20.0 | 2.5 |
| 1.3% Benzophenone | 1 | 2.5 | 50 | 5.0 | 0.8 |
|  | 2 | 4.9 | 39 | 7.1 | 1.1 |
|  | 3 | 6.2 | 36 | 9.4 | 1.5 |
|  | 4 | 7.3 | 28 | 11.0 | 1.7 |

EXAMPLE 4

The experiments of Example 2 were repeated using a TEFLON cell in an effort to reduce the wall reaction. Table 4 shows that the cumene oxidation rate and selectivity to cumene hydroperoxide were increased in the TEFLON cell as compared to that in the uncoated aluminum cell of Example 2, indicating that the wall reaction was minimized. The addition of benzophenone (1.5 wt.%) was shown to increase the rate of oxidation. The selectivity to cumene hydroperoxide, however, remained nearly the same when compared to that without the promoter for the same conversion.

TABLE 4

Cumene Oxidation in TEFLON Cell

|  | Time, hr | Conversion, % | Hydroperoxide Selectivity, % |
|---|---|---|---|
| No additive | 1.0 | 0.42 | 100 |
|  | 2.0 | 1.4 | 100 |
|  | 3.0 | 3.0 | 98 |

TABLE 4-continued

Cumene Oxidation in TEFLON Cell

|  | Time, hr | Conversion, % | Hydroperoxide Selectivity, % |
|---|---|---|---|
|  | 4.0 | 4.6 | 98 |
| 1.5% Benzophenone | 1.0 | 0.54 | 100 |
|  | 2.0 | 1.7 | 98 |
|  | 3.0 | 4.9 | 95 |
|  | 4.0 | 8.3 | 93 |

EXAMPLE 5

The experiment of Example 2 was repeated using acetaphenone and 9-fluorenone in place of the benzophenone promoter. The acetophenone and 9-fluorenone were added to the cumene feed in the amount of 1 wt.% and 0.6 wt.%, respectively. Table 5 demonstrates that acetophenone only slightly increases the oxidation rate of cumene; but 9-fluorenone does not enhance the rate in comparison to the non-additive case in Table 2.

TABLE 5

CUMENE OXIDATION WITH ACETOPHENONE AND 9-FLUORENONE

|  | Time, Hr. | Conversion |
|---|---|---|
| 1% ACETOPHENONE | 3.0 | 0.99 |
| 0.6% 9-FLUORENONE | 3.0 | 0.88 |

Having thus described the invention, it should be apparent that variations in amounts and reactants and conditions of operation would be readily apparent to one having ordinary skill in this art and those variations would be within the spirit of the invention as set forth in the appended claims.

We claim as our invention:

1. A process for the production of hydroperoxides comprising the steps of:

adding an oxygen-containing gas to a feed hydrocarbon selected from the group consisting of cumene, ethylbenzene, isobutane and cyclohexane in the presence of a promoter ketone selected from the group consisting of benzophenone, ortho-$(NO_2)(C_6H_4)_2C=O$, (meta-$(NO_2)$ $(C_6H_4)_2C=O$, $(C_6F_5)_2C=O$ and $(C_6F_3)_2C=O$ which ketone results in a reaction rate to a corresponding hydroperoxide higher than the reaction rate occurring with acetophenone upon hydrocarbon at the same conditions, at a temperature between 100 and 200 C. to produce a corresponding hydroperoxide product, and recovering the corresponding hydroperoxide product.

2. The process of claim 1 wherein the promoter ketone is benzophenone.

* * * * *